United States Patent [19]

Naipawer

[11] Patent Number: 4,696,766

[45] Date of Patent: Sep. 29, 1987

[54] (2R*,3S*)-(E)-3-METHYL-5-(2,2,3-TRIMETHYLCYCLOPENT-3-EN-1-YL)PENT-4-EN-2-OL

[75] Inventor: Richard E. Naipawer, Wallington, N.J.

[73] Assignee: Givaudan Corporation, Clifton, N.J.

[21] Appl. No.: 841,500

[22] Filed: Mar. 19, 1986

[51] Int. Cl.$^4$ .......................... A61K 7/46; C11B 9/00; C07C 35/06
[52] U.S. Cl. ...................... 512/8; 568/838; 568/330
[58] Field of Search ................ 252/522 R; 568/330, 568/838

[56] References Cited

U.S. PATENT DOCUMENTS

| | | | |
|---|---|---|---|
| 3,978,009 | 8/1976 | Schulte-Elte | 252/522 R |
| 4,052,341 | 10/1977 | Naipawer et al. | |
| 4,149,020 | 4/1979 | Kamath et al. | 252/522 R |
| 4,170,577 | 10/1979 | Kamath et al. | 252/522 R |
| 4,173,585 | 11/1979 | Yoshida et al. | |
| 4,174,287 | 11/1979 | Kamath et al. | 252/522 R |
| 4,206,091 | 6/1980 | Yoshida | 252/522 R |
| 4,208,296 | 6/1980 | Yoshida et al. | 252/522 R |
| 4,219,451 | 8/1980 | Yoshida et al. | 252/522 R |
| 4,278,569 | 7/1981 | Yoshida et al. | 252/522 R |

OTHER PUBLICATIONS

E. -J. Brunke, et al., "Fragrance Chemistry-The Science of the Sense of Smell", E. T. Theimer ed., Academic Press, New York (1982) p. 397.
J. E. Amoore, ibid., p. 34.
H. O. House, "Modern Synthetic Reactions, 2nd Ed., W. A. Benjamin Inc., Menlo Park, CA (1972) p. 644.
H. J. Ringold, et al., Tet. Lett., No. 15, 669 (1962).
E. D'Incan, et al., Tetrahedron 40, 3421 (1984).
J. Rigaudy, et al., "Nomenclature of Organic Chemistry", 1979 Edition, Pergamon Press, New York, p. 482.
F. Zobrist et al., Helv. 35, 2380 (1952).
L. Fieser et al., "Reagents for Organic Synthesis", vol. I, John Wiley and Sons, Inc., New York, p. 170.
K. H. Shankaranarayana, et al., Perf. and Flav. 9, 17, (1984).
E. -J. Brunke, et al., Dragoco Report (Engl. Frag. Ed.) No. 5, p. 67 (1980).
E. -J. Brunke, ibid., No. 8, p. 187 (1981).

*Primary Examiner*—Werren B. Lone
*Attorney, Agent, or Firm*—Robert F. Tavares; Linda A. Vag

[57] ABSTRACT

(2R*,3S*)-(E)-3-Methyl-5-(2,2,3-trimethylcyclopent-3-en-1-yl)pent-4-en-2-ol possesses a very intense creamy, woody, musk, sandalwood odor and is a valuable ingredient for use in fragrance compositions for its musk and sandalwood-like qualities. This odorant is more intense than any of the campholenic aldehyde derivatives that have been previously reported.

27 Claims, No Drawings

(2R*,3S*)-(E)-3-METHYL-5-(2,2,3-TRIMETHYLCYCLOPENT-3-EN-1-YL)PENT-4-EN-2-OL

This is a continuation-in-part of Ser. No. 740,467 filed May 31, 1985.

BACKGROUND OF THE INVENTION

East Indian sandalwood oil has been described as being "perhaps one of the most precious perfumery materials from antiquity down to modern times, and its popularity has shown no signs of waning" [E. Guenther, "The Essential Oils", Vol. V, Page 173, D. Van Nostrand Company, Incorporated, New York (1952)]. This oil is widely used in perfumery and would be even more widely used except for its limited supply and high cost.

For many years a need existed for synthetic substitutes which could be used as sandalwood substitutes or as extenders. In 1977 Naipawer and Easter (U.S. Pat. No. 4,052,341) disclosed the compound 3-methyl-5-(2,2,3-trimethylcyclopent-3-en-1-yl)pentan-2-ol which was characterized by a tenacious fine soft woody odor similar to sandalwood oil and the naturally occurring santalols. This compound not only has a fine sandalwood odor, it is also more stable than the potentially labile allylic alcohols of beta- and alpha-santalol. [Naipawer and Easter also disclosed and claimed the unsaturated analog 3-methyl-5-(2,2,3-trimethylcylopent-3-en-1-yl)pent-3-en-2-ol]. A major advantage of this invention is the fact that the compound can be readily and economically prepared from inexpensive materials, i.e., campholenic aldehyde and 2-butanone (methyl ethyl ketone). Campholenic aldehyde, which is readily available from alpha-pinene epoxide, is a relatively inexpensive starting material.

After the Naipawer and Easter patent appeared, there was a flurry of activity in this area and a number of patents appeared claiming sandalwood-type odorants starting from campholenic aldehyde. In most instances, these patents differed from one another in the compound that was condensed with campholenic aldehyde, the manner in which the condensation was conducted or the chemical steps that were performed on the condensation product.

The activity of the analysis of sandalwood oil and the search for synthetic substitutes has been thoroughly reviewed. (See E. -J. Brunke and W. Rojahn, Dragoco Report (Engl. Frag. Ed.), No. 5, 67, (1980); E. -J. Brunke, ibid., No. 8, 187, (1981), E. -J. Brunke and E. Klein in "Fragrance Chemistry-The Science of the Sense of Smell", E. T. Theimer, Ed., Academic Press, New York, N.Y., 1982, pp 397–431; K. H. Shankaranarayana and K. Parthasarathi, Perfumer and Flavorist, 9, 17, (1984); and other references mentioned in those reviews.)

Based on a reading of the above review articles and the patents issued, it would appear that the prior art has exhaustively covered all of the more valuable odorants that could be made starting from campholenic aldehyde. Applicant, however, discloses herein the most intense and most valuable campholenic aldehyde derivative that has been reported to date, a derivative that has escaped characterization and appreciation by all the investigators who have exhaustively studied and reviewed this field.

THE INVENTION

The invention is more clearly understood by considering the sequence of steps outlined in Chart I which represents the most economical route for the preparation of what appears to be the most powerful odorant of this type ever prepared. [The asterisk (*) indicates an asymmetric center.]

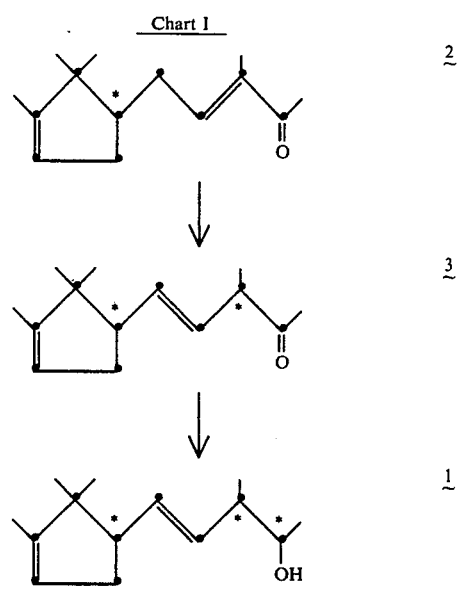

Compound 2 is a α,β-unsaturated ketone which can be prepared as described in U.S. Pat. No. 4,052,341. It can be isomeric about the double bond (E or Z) and has one asymmetric center which is designated by the asterisk (*). This compound (2) can be converted to the β,γ-unsaturated ketone 3 by forming the enolate and protonating under conditions that give the kinetically favored product.

The configuration about the double bond in compound 3 is trans or E as indicated. The conversion of 2 to 3 introduces a second asymmetric center, also indicated by an asterisk (*). There are expected two possible diastereomers, i.e. two pairs of enantiomers (two d,l pairs) for the ketone 3. While the diastereomers have not been separated on gas-liquid chromatography (GLC) (Carbowax® 20M capillary column), the $^{13}$C-NMR provides evidence that both diastereomers are present.

Compound 3 can be converted to compound 1 by reducing the ketone carbonyl to the corresponding alcohol. This process introduces a third asymmetric center (*) which means that four diastereomers (four pairs of enantiomers or d,l pairs) are now expected. In this instance, gas-liquid chromatography (Carbowax® 20M capillary column) separates the product into two peaks. These two components are also separated by spinning band distillation. The component which is lower boiling and which elutes first on a Carbowax® 20M capillary GLC column is hereinafter referred to as component 1a. The component which is higher boiling and which elutes last on a Carbowax® 20M capillary GLC column is hereinafter referred to as component 1b. While each of these two components appears to be pure on the Carbowax® 20M capillary column, gas-liquid chromatographic analysis on an ethylene glycol succinate capillary column (LAC-4R-886) resolves each of these into two peaks. Therefore all four possible diastereomers (d,l pairs) are present. $^{13}$C-NMR and $^1$H-NMR (400 MHz) confirm the presence of the four diastereomers.

It is expected that two of the diastereomers would possess the anti (or threo) relative configuration with respect to the adjacent asymmetric centers at carbons 2 and 3, while the other two would possess the syn (or erythro) relative configuration with respect to these two asymmetric centers.

Based on an examination of the 400 MHz $^1$H-NMR spectra of components 1a and 1b, it has been concluded that the two diastereomers present in 1a are of similar relative configuration as to the two adjacent asymmetric centers. A similar conclusion has been made as to the diastereomers present in 1b. This conclusion is based on the fact that the spectrum for 1a shows a series of double peaks for the methyl groups on the side-chain, i.e. these methyl groups have nearly identical chemical shifts. The spectrum for component 1b also shows a series of such doublets, but the side-chain methyl groups in 1b have chemical shifts that are quite different from the corresponding chemical shifts for the side-chain methyl groups in 1a. Based on the differences in the chemical shifts for the side-chain methyl groups it can be concluded that the side-chains in 1a have different relative configurations from the side chains in 1b i.e., one is anti and one is syn.

X-ray diffraction crystallographic analysis of crystalline esters of component 1a and of component 1b were utilized to determine the relative configuration at the side-chains in each component and the relative stereochemical configuration of the four diastereomers.

The first eluting diastereomer of component 1a (GLC on LAC-4R-886) produced a crystalline allophanate derivative suitable for X-ray diffraction crystallographic analysis. The diffraction pattern showed that this diastereomer possessed the anti relative configuration with respect to carbons 2 and 3 since tne relative stereochemical configurations at these carbon atoms were determined to be R* and S*, respectively. The pattern also showed that the relative stereochemical configuation at ring carbon 1 was S*. The first component of 1a was therefore the (2R*,3S*)-(E)-3-methyl-5-(2,2,3-trimethylcyclopent-3-en-1(S*)-yl)pent-4-en-2-ol diastereomer (d,l pair). Based on the $^1$H-NMR data (discussed above) indicating that both diastereomers present in 1a were of similar relative configuration at the side-chain, the second diastereomer of component 1a also possessed the anti relative configuration with respect to carbons 2 and 3 and was therefore the (2R*,3S*)-(E)-3-methyl-5-(2,2,3-trimethylyclopent-3-en-1(R*)-yl)pent-4-en-2-ol diastereomer (d,l pair).

The first eluting diastereomer of component 1b (GLC on LAC-4R-886) produced a crystalline carbamate derivative suitable for X-ray diffraction crystallographic analysis. The diffraction pattern showed that this pair possessed the relative stereochemical configuration at carbons 2 and 3 of R* and R* respectively. This diastereomer would therefore have the syn relative configuration with respect to these two carbon atoms. The diffraction pattern also showed that the relative stereochemical configuration at ring carbon 1 was R*. The first component of 1b was therefore the (2R*,3R*)-(E)-3-methyl-5-(2,2,3-trimethylcyclopent-3-en-1(R*)-yl)pent-4-en-2-ol diastereomer (d,l pair). Based on the $^1$H-NMR data (discussed above) indicating that both pairs present in 1b were of similar relative configuration at the side-chain, it was concluded that the second diastereomer of component 1b also possessed the syn relative configuration at carbons 2 and 3 and was therefore the (2R*,3R*)-(E)-3-methyl-5-(2,2,3-trimethylcyclopent-3-en-2(S*)-yl)pent-4-en-2-ol diastereomer (d,l pair).

Therefore, 1a designates the diastereomers of compound 1 which are lower boiling, elute first on a Carbowax ® 20M capillary column, and which possess the anti or R*,S* relative configuration at carbons 2 and 3, i.e. the (2R*,3S*)-(E)-3-methyl-5-(2,2,3-trimethylcyclopent-3-en-1-yl)pent-4-en-2-ol isomers. Similarly 1b designates the diastereomers of compound 1 which are higher boiling, elute last on a Carbowax ® 20M capillary column, and which possess the syn or R*,R* relative configuration at carbons 2 and 3, i.e., the (2R*,3R*)-(E)-3-methyl-5-(2,2,3-trimethylcyclopent-3-en-1-yl)pent-4-en-2-ol isomers.

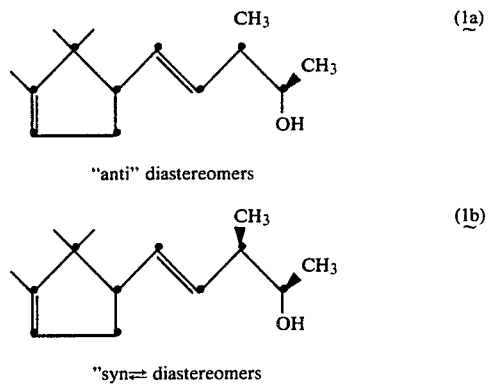

"anti" diastereomers (1a)

"syn" diastereomers (1b)

The component designated as 1a is the campholenic aldehyde derivative having the strongest odor ever reported. It has about four hundred times the odor intensity, as determined by odor threshold values, of natural santalol and has about five hundred times the odor intensity of component 1b. (The odor threshold is a physical property of the composition and is defined as being "its lowest concentration in air that can be consistently distinguished from pure air" [J. E. Amoore, "Fragrance Chemistry-The Science of the Sense of Smell", E. T. Theimer, Ed., Academic Press, New York, N.Y., 1982, pp 34–41]. The odor threshold value is expressed in terms of the weight of odorant per unit volume of air as determined by olfactometry, a technique known to those skilled in the art and discussed by Amoore. In essence, odor threshold value is the smallest amount of odorant that must be present in a unit volume of air to be detected, i.e., distinguished from the air itself).

This invention illustrates the importance that the stereochemical configuration plays in the odor properties of these alcohols. At the heart of this invention is the fact that the relative configuration around the asymmetric centers in the homoallylic alcohol (E)-3-methyl-5-(2,2,3-trimethylcyclopent-3-en-1-yl)pent-4-en-2-ol appears to be critical with regard to odor intensity. As reported above, one component (1a) appears to have an odor intensity as shown by threshold values of over five hundred times the odor intensity of the other component (1b).

The present invention is drawn to the novel components 1a and 1b which have been assigned structures as indicated above, to novel compositions containing 1a and/or 1b, to the use of these in odorant compositions and to the intermediate ketone 3.

DESCRIPTION OF THE PREFERRED EMBODIMENTS

As indicated in Chart I, the mixture of isomers of (E)-3-methyl-5-(2,2,3-trimethylcyclopent-3-en-1-yl)pent-4-en-2-ol (1) can be prepared by converting the α,β-unsaturated ketone 2 to the β,γ-unsaturated ketone 3 and subsequently converting the carbonyl group of 3 to an alcohol. The compound 2 can be prepared in a variety of ways, two of which are illustrated in Chart II below. [The asterisk (*) is used in Chart II and throughout this text to indicate a pertinent asymmetric center.]

The scope and limitations of this invention as well as the preferred embodiments of this invention are best understood by following the scheme as outlined in Chart II since the novel compositions reported herein which contain 1a may contain other isomers which result from the particular process used.

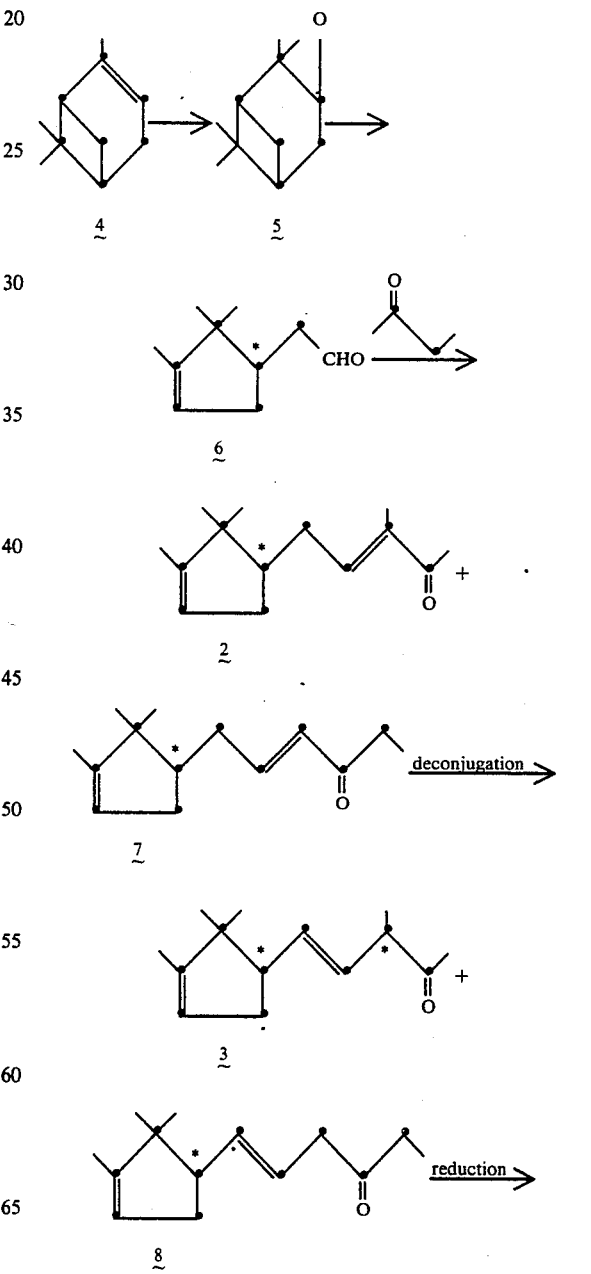

-continued
Chart II

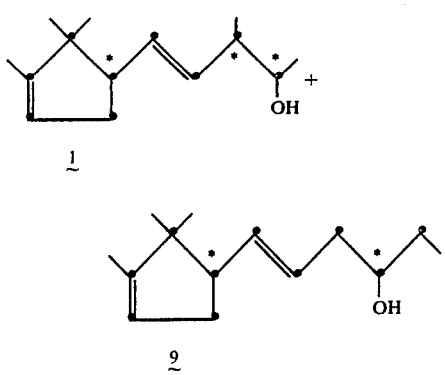

Chart II shows two possible routes to compositions containing compound 1, i.e. the mixture of diastereomers of (E)-3-methyl-5-(2,2,3-trimethylcyclopent-3-en-1-yl)pent-4-en-2-ol. Campholenic aldehyde (6) is the common starting material for both Path A and Path B and is prepared from α-pinene (4) via the epoxide 5, as shown in Chart II. This is a process well known in the art. See for example U.S. Pat. No. 4,052,341.

Path A differs from Path B in that a different compound is used in the aldol condensation with the campholenic aldehyde. The former uses propanal and the latter uses 2-butanone. Path A has the advantage that the condensation product 10 can be converted to the α,β-unsaturated ketone 2 without forming, at the same time, small amounts of the ethyl ketone 7. Path B, however, is much more economical to carry out than Path A since Path B requires fewer and less expensive steps. These economic advantages make Path B the preferred route even though some of the ethyl ketone 7 would be formed during the condensation of campholenic aldehyde and 2-butanone. (The ethyl ketone 7 is eventually converted to the alcohol 9 which, as will be shown below, has little effect on the odor quality of the final product.)

In Path A, the condensation of campholenic aldehyde and propanal can be carried out as described in Example IV-1 of U.S. Pat. No. 4,052,341 to form the desired 2-methyl-4-(2,2,3-trimethylcyclopent-3-en-1-yl)but-2-enal (10). The aldehyde 10 can then be converted to the alcohol 11 using methylmagnesium halide or methyllithium in a Grignard-type reaction. The alcohol 11 can then be oxidized to the pure ketone 2 which is free from any of the ethyl ketone isomer 7. The ketone 2 can be deconjugated to 3 which in turn can be reduced to the alcohol 1 as described below in the discussion of the preferred route, Path B.

In Path B the aldol condensation between campholenic aldehyde and 2-butanone may take place at either of the carbon atoms adjacent to the carbonyl and may produce a mixture of products. It is expected that an aldehyde will preferentially react with the more reactive methylene group than with the less reactive methyl. The relative amounts of methyl ketone or ethyl ketone formed may be dependent on variables such as the reaction temperature, reaction time and catalyst used.

Using the conditions described in U.S. Pat. No. 4,052,341, the ratio of compound 2 to compound 7 is about ten to one. It has been found that if the ketone 7 is carried through the sequence of steps, the compound formed, i.e. the 6-(2,2,3-trimethylcyclopent-3-en-1-yl)hex-5-en-3-ol (9), has an odor which is much weaker than and compatible with the odor of 1a, and therefore there is no need to separate the ten to one mixture of 2 and 7 before proceeding.

In the aldol condensation between campholenic aldehyde and 2-butanone, shown in Path B, a β-hydroxyketone intermediate is formed which is capable of dehydrating to produce either the α,β-unsaturated ketone 2 or the β,γ-unsaturated ketone 3. The α,β-unsaturated ketone 2 is usually the major or exclusive product. (The amount of the β,γ-unsaturated ketone that may be produced is usually dependent on variables such as reaction temperature, reaction time, catalyst and substituent groups present on the aldehyde and/or the ketone being condensed. (See H. O. House, "Modern Synthetic Reactions", 2nd ed. W. A. Benjamin, Inc., Menlo Park, CA., 1972, pp 644–645.).

Once the ketone 2 has been obtained via Path A or Path B, it can be converted to the β,γ-unsaturated ketone 3 by any means known in the art for moving double bonds out of conjugation [H. J. Ringold and S. K. Malhotra, Tet. Letters, No. 15, 669 (1962); E. D'Incan and P. Viout, Tetrahedron, 40, 3421 (1984)]. All these methods rely on the initial formation of an enolate followed by the protonation of that enolate under conditions that provide the kinetically favored product in excess over the thermodynamically favored product.

While most of the conditions for converting an α,β-unsaturated ketone to the corresponding β,γ-unsaturated ketone should be suitable, it is preferred to use conditions that minimize undesirable side reactions such as self-condensation of the ketones and isomerization of the kinetically favored β,γ-unsaturated product back into the thermodynamically favored α,β-unsaturated starting material.

In the preferred process of this invention, the ketone to be isomerized is slowly added to a solution of a suitable base (e.g. an alkali metal tertiary alkoxide) in an appropriate aprotic solvent at a temperature of about 10° C. to 30° C. The rate of addition would be determined by one skilled in the art depending on the size of the reaction, the productivity required and the amount of self-condensation that can be tolerated. For laboratory-size batches, an addition time of one hour is suitable.

The temperature of the enolate formation is not critical. Temperatures above 30° C. tend to produce more condensation side products and temperatures below 10° C. do not offer a sufficient advantage to justify the need for the additional cooling. Once the addition is complete, the reaction is continued at 10° C. to 30° C. for an additional time until the enolate formation is complete. (Completion of enolate formation can be determined by the workup of a small sample and analysis of the products by gas-liquid chromatography.)

As the base used for the isomerization, it is preferred to use an alkali metal tertiary alkoxide such as potassium t-butoxide, sodium t-butoxide, the corresponding t-amylates or the like. The readily available and more economical potassium t-butoxide is preferred. It is preferred to use an excess of the base (20–80%) with an excess of about 40% to 60% being especially preferred.

The solvent used is limited to aprotic, anhydrous solvents which are capable of solvating the t-alkoxides and the enolate formed. Typical solvents normally used for this purpose are ethers, polyethers, N,N-dialkylamides and the like. Preferred solvents are the commercially available 1,2-dimethoxyethane (DME), diethylene glycol dimethyl ether (Diglyme), N,N-dimethylacetamide (DMAC) and N,N-dimethylformamide (DMF), with DMF being especially preferred.

Once the enolate has been formed, it can be protonated to the β,γ-unsaturated ketone by means of a suitable proton source which will allow the kinetic product (the β,γ-unsaturated ketone) to be formed without reverting to the α,β-unsaturated ketone. While a number of proton sources should be suitable, it has been found that excellent results can be obtained by either adding aqueous acetic acid to the reaction mixture or by adding the reaction mixture to aqueous acetic acid. The β,γ-unsaturated ketone is obtained in 75–85% yields and contains less than 5% of the starting α,β-unsaturated ketone. (Since the neutralization is exothermic, it is preferred to use cold aqueous acetic acid.) The desired β,γ-unsaturated ketone can be separated from the small amount of the higher boiling α,β-unsaturated ketone present by fractional distillation. (The presence of small amounts of the α,β-unsaturated ketone 2 is not detrimental since it is converted to a mixture of 3-methyl-5-(2,2,3-trimethyl-cyclopent-3-en-1-yl)-pentan-2-ol (12) and 3-methyl-5-(2,2,3-trimethylcyclopent-3-en-1-yl)pent-3-en-2-ol (11), both of which have odors that are compatible with the desired product.

If the α,β-unsaturated ketone 2 was prepared by Path A, the β,γ-unsaturated ketone 3 is free of any of the compound 8, and can be obtained in extremely pure form. If the α,β-unsaturated ketone 2 was prepared by Path B, and contained the ethyl ketone 7, the ethyl ketone present will be isomerized to the β,γ-unsaturated ketone 8. It has been found, however, that the enolate of the β,γ-unsaturated ketone 8 forms self-condensation products much more rapidly than does the β,γ-unsaturated ketone 3 under basic conditions. It has also been found, that if the isomerization is carried out a little longer or at somewhat higher temperatures, ca. 40°–60° C., the β,γ-unsaturated ketone 8 present will consume itself via self-condensation. By following the reaction by GLC, the reaction can be run until the only β,γ-unsaturated ketone present is compound 3 and virtually none of the compound 8 is present. Thus one can prepare pure 3 even though Path B is used.

The β,γ-unsaturated ketone obtained via either Path A or Path B can be converted to the corresponding homoallylic alcohol by reducing the carbonyl group to a hydroxyl group. The reduction can be suitably carried out using a metal hydride such as lithium aluminum hydride, sodium borohydride, sodium bis(2-methoxyethoxy)aluminum hydride, etc., with sodium borohydride being preferred because of economic considerations and ease of handling.

The product resulting from the reduction, as mentioned earlier, is primarily a mixture of diastereomers having the structure 1. The three asymmetric centers of compound 1 allow for the existence of four pairs of enantiomers, i.e., four d,l pairs.

Gas-liquid chromatographic analysis (Carbowax ® 20M, fused silica capillary) shows only two peaks present in approximately a 7 to 5 ratio, each peak of which can be isolated pure by a careful distillation, e.g. a spinning band distillation. These two components have been designated as 1a and 1b, respectively. GLC analysis on an ethylene glycol succinate (LAC-4R-886) capillary column shows that 1a and 1b are each composed of two peaks (each in an approximate 1 to 1 ratio) indicating that all four possible diastereomers are present. [$^{13}$C-NMR and $^1$H-NMR (400 MHz) also confirm the presence of all four possible diastereomers.]

As mentioned earlier, it has been determined from X-ray diffraction crystallographic analysis and $^1$H-NMR (400 MHz) that the two diastereomers denoted by 1a possess the anti or R*,S* relative configuration at the two asymmetric centers in the side-chain (carbons 2 and 3), while the two diastereomers denoted by 1b possess the syn or R*,R* relative configuration at these carbons.

Alcohol 1a therefore denotes the more abundant component which has the lower boiling point, elutes first on a Carbowax ® 20M capillary GLC column, and contains the two diastereomers assigned the anti or R*,S* stereochemical configuration in the side-chain, i.e. the (2R*,3S*)-(E)-3-methyl-5-(2,2,3-trimethylcyclopent-3-en-1-yl)pent-4-en-2-ols. Alcohol 1b denotes the less abundant component which has the higher boiling point, elutes second on a Carbowax ® 20M capillary GLC column, and contains the two diastereomers assigned the syn or R*,R* stereochemical configuration in the side-chain, i.e. the (2R*,3R*)-(E)-3-methyl-5-(2,2,3-trimethylcyclopent-3-en-1-yl)pent-4-en-2-ols.

In evaluating the odor properties of the alcohol 1 it was observed that component 1a had an odor of unexpected intensity, particularly in comparison to related sandalwood-like odorants known in the prior art and also in comparison to component 1b. These differences were shown by subjecting a number of odorants to an olfactometric determination of their respective odor threshold values.

The relative odor threshold values of alcohols 1a and 1b, and related odorants known in the prior art were determined by standard olfactometric methods known to one skilled in the art. These values ae tabulated in Table I. The values are relative to the saturated compound 12 which was assigned a value of 1.0.

TABLE I

| Odorant | Relative Odor Threshold |
|---|---|
| 1a | 0.003 |
| 1b | 1.5 |
| 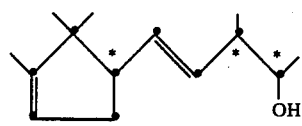 α-Santalol | 1.17 |

TABLE I-continued

| Odorant | Relative Odor Threshold |
|---|---|
| 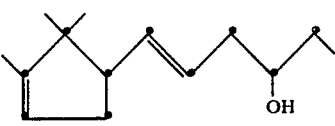 9 | 7.83 |
| 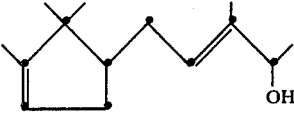 11 | 0.13 |
| 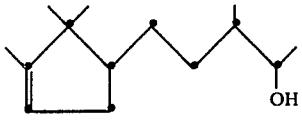 12 | 1.0 |

The above relative odor threshold values show the unexpected and unpredictable superiority of 1a. The odor of alcohol 1a is approximately 300 times more intense than the odor of 12, which, as discussed previously, is an intense sandalwood odorant of good stability. The odor of component 1a is approximately 400 times more intense than the odor of α-santalol and approximately 40 times more intense than the odor of the corresponding α,β-unsaturated alcohol 11. Even more surprising and unexpected is the fact that the odor of 1a is more than 500 times as intense as the odor of its sister diastereomeric alcohol 1b.

While pure 1a would be the strongest sandalwood-type odorant ever discovered, it is not economical to separate this component from 1b. Fortunately 1b is a much weaker odorant, 500 times weaker with respect to odor threshold value, and does not interfere with the odor properties of 1a. In the mixture of 1a and 1b, the 1b is essentially a diluent.

It is because of the extreme odor intensity of 1a, it being several orders of magnitude more powerful than any of the other isomers shown in Table I, that mixtures containing 1b, 9, 11 or 12 need not be separated. For example, since it takes five hundred times more of 1b to be detected in air than 1a, a mixture which is about 60% 1a and about 40% 1b is going to have an odor which is very similar to pure 1a. The same is true for any amount of isomers due to the use of Path B, e.g., compound 9 which may have resulted from the presence of ketone 7 due to aldol condensation on the methyl group of 2-butanone. Since Table I shows that there must be over a thousand times more compound 9 than 1a to be detectable in air, then even if compound 9 is present in about ten percent, there will be no detrimental effect on the odor of the mixture and that odor will be very similar to the odor of pure 1a.

Even if there was some α,β-unsaturated ketone 2 present with the β,γ-unsaturated ketone 3 after the isomerization step, this would be converted to the saturated pentanol 12, and the allylic alcohol 11. Both of these compounds are fine and strong odorants, but small amounts would not discernably detract from the odor value of 1a.

The novel compositions of this invention comprise, therefore, any compositions wherein the content of 1a is greater than ten percent of the total composition. The preferred compositions of this invention are those compositions wherein 1a is greater than twenty-five percent of the total, with those compositions having greater than forty percent 1a being highly preferred. Especially preferred are those compositions wherein the amount of 1a present is greater than fifty percent.

Among the especially preferred compositions are those consisting essentially of
(a) fifty to one hundred percent 1a
(b) zero to forty-five percent 1b
(c) zero to twelve percent compound 9
(d) zero to ten percent compound 11
(e) zero to ten percent compound 12.

As mentioned earlier, it is not economically practical to separate 1a and 1b so that the commercially successful product will be a mixture of these two components. Said mixtures will consist essentially of
(a) forty to sixty-five percent 1a
(b) twenty-five to forty-five percent 1b
(c) zero to twelve percent compound 9
(d) zero to five percent compound 11
(e) zero to five percent compound 12

The reason that these novel components are so valuable in perfumery is due to their very intense and unique odor properties. Alcohol 1a is characterized not only as sandalwood-like, but as having qualities that make it even more valuable. Its unique odor can be characterized as a powerful, creamy, woody, musk, sandalwood odor. The unique intensity along with the musk quality gives 1a a value possessed by no other substance or combination of substances and makes it a uniquely valuable odorant in a variety of fragrance types such as woody compositions, musk-like compositions, floral compositions, chypre accords, citrus accords and the like. Alcohol 1a lends to these fragrances the natural quality usually found only when the more expensive natural oils are used, yet it is unique in its own right and cannot be replaced by any natural oil or combination thereof. Since the intensity of 1a is so strong, the composition consisting of 1a plus 1b or compositions of 1a plus 1b which also include some amounts of 9 and/or 12 and/or 11 can be used with practically the same effect as pure 1a. The odor of 1a dominates these compositions. The other isomers (1b, 9, 11, 12) affect the mixture only by reducing its intensity, in effect, acting as diluents.

The addition of the novel compositions of this invention containing 1a to fragrance compositions results in dramatic improvements in a number of fragrance types. A number of illustrations showing the value of the compositions of this invention are given in Example VI. In this example, compositions of this invention were added such that the amount of 1a present in the final fragrance mixture was from about 0.15% to 2.5%. The effects were dramatic and could not be achieved by substituting similar amounts of sandalwood oil or any of the other odorants shown in Table I.

In fragrance compositions of the woody type (precious woody or cedar-like) one can use the novel compositions of this invention containing 1a in larger amounts to add a distinctive and dominant note, or in smaller amounts to provide a rounding or blending effect. The compositions of this invention can be used similarly in large amounts in musk-like compositions to provide unique and highly desirable characteristics.

In floral type compositions, the use of small amounts of the novel compositions of this invention is found to contribute in a way that results in a rounder, warmer and better blended fragrance. In citrus accords, the addition of small amounts of the compositions of this invention adds an interesting musky note to these accords. The compositions of this invention have also been shown to enhance the woody notes of a chypre accord.

The novel compositions of this invention containing 1a can be used in a variety of applications. The amounts used and the scope of such use will depend solely on the imagination and personal preferences of each perfumer.

For the most part, the novel compositions of this invention can be used in fragrance formulations in an amount such that the amount of 1a present in the final fragrance mixture can range from as low as 0.005% to 5% with 0.15% to 2.5% being preferred. This will vary, of course, depending upon the type of fragrance formula involved. Concentrations above 5%, even as high as 80 or 90%, may be used successfully for special effects.

The novel compositions of this invention can be used to prepare fragrance bases for the preparation of perfumes and toilet waters by adding the usual alcoholic and aqueous diluents thereto. Approximately 15–20% by weight of base would be used for perfumes and approximately 3–5% for toilet waters.

Similarly, the base compositions can be used to odorize soaps, detergents, cosmetics or the like. In these instances, a base concentration of from about 0.1% to about 2% by weight can be used.

ILLUSTRATION OF THE PREFERRED EMBODIMENTS

The following examples are provided to illustrate the preferred embodiments as they are disclosed herein and are not to be construed as limiting.

Infrared spectra (IR) were recorded as neat samples using a Perkin-Elmer Model 681 spectrophotometer and absorptions are reported in inverse centimeters ($cm^{-1}$).

Molecular weights were determined by electron impact mass spectroscopy using a Finnigan Model 4000 quadrapole mass spectrometer.

Nuclear magnetic resonance (NMR) spectra were recorded as solutions in chloroform-$d_1$, using a Varian Em-360 proton spectrometer ($^1$H-NMR) operating at 60 MHz, a Brüker Model WH-400 heteronuclear spectrometer ($^1$H-NMR) operating at 400 MHz and a Varian Model CFT-20 heteronuclear spectrometer ($^{13}$C-NMR), and are reported as $\delta$ units relative to tetramethylsilane (TMS) (0.0$\delta$). Unless otherwise indicated. $^1$H-NMR spectra were recorded on the Varian Model EM-360 spectrometer operating at 60 MHz.

Unless otherwise indicated gas-liquid chromatography (GLC) was carried out on a Carbowax ®20M (registered trademark of Union Carbide Corp. for polyethylene glycol) fused silica capillary column (0.25 mm × 30 meters) using a Hewlett-Packard Model 5880A gas chromatograph with a flame ionization detector (FID). Non-routine GLC, where indicated, was carried out on an LAC-4R-886 (ethylene glycol succinate) capillary column (0.30 mm × 39 meters).

Unless otherwise indicated weights are in grams, temperatures are in degrees centigrade, pressures are in mm Hg and yields are based on theory.

EXAMPLE I

Preparation of
(E)-3-Methyl-5-(2,2,3-trimethycyclopent-3-en-1-yl)pent-4-en-2-one (3)

The $\alpha,\beta$-unsaturated ketone used as starting material in this example was obtained according to Example II-1 of U.S. Pat. No. 4,052,341 and consists primarily of 3-methyl-5-(2,2,3-trimethylcyclopent-3-en-1-yl)pent-3-en-2-one (2) (82%) and 6-(2,2,3-trimethylcyclopent-3-en-1-yl)hex-4-en-3-one (7) (6–8%) and small amounts of the corresponding $\beta,\gamma$ isomers 3, (4%) and 8, (4%).

Potassium t-butoxide (33.6 g, 0.30 mole) was added to a reaction flask containing 150 ml of N,N-dimethylformamide (DMF). The mixture was stirred and was cooled to 15° C. The $\alpha,\beta$-unsaturated ketone (41.2 g, 0.2 mole) was added slowly over 1.0 hour at 15°–25° C., with cooling being applied as necessary in order to maintain the temperature within this range. The resultant solution was stirred at ambient temperature for an additional period of 4.0 hours.

The mixture was cooled to 0° C. and 150 ml of aqueous 20% acetic acid was added rapidly. The mixture was stirred for 15 minutes, was then poured into a beaker containing 150 ml of water and was extracted with three 100-ml portions of toluene. The toluene extracts were combined and were washed with two 100-ml portions of 10% sodium bicarbonate solution and then with one 100-ml portion of water.

The washed toluene layer was dried over anhydrous magnesium sulfate, filtered and the toluene removed by distillation at reduced pressure (ca. 100 mm). The oil remaining was distilled at reduced pressure (0.5 mm) to yield 34.8 g (84.5% yield of (E)-3-methyl-5-(2,2,3-trimethylcyclopent-3-en-1-yl)pent-4-en-2-one (3) (86%) and the isomeric ethyl ketone 8 (9%): bp 73°–86° C. (0.5 mm); mol. wt. 206 (MS); IR 1725 $cm^{-1}$ (carbonyl), 805 $cm^{-1}$ (trisubstituted olefin).

$^1$H-NMR 0.8$\delta$(3H, s), 1.0(3H, s), 1.2(3H, d, J~7.5 Hz), 1.6(3H, broad s, olefininc CH$_3$), 2.2(3H, s, acetyl CH$_3$), 1.9–2.5(3H, broad complex), 3.2(1H, broad multiplet, J~7.5), 5.2(1H, broad multiplet, olefinic H), 5.4–5.9(2H, complex).

$^{13}$C-NMR 121.5 ppm(d) and 147.8(s) representing 2 ring olefinic carbons; 129.9(d) and 134.2+134.5(2d) representing 2 olefinic carbons; 209.3(s, carbonyl). The $^{13}$C-NMR indicates 14 distinct carbon resonances with 7 carbon resonances appearing as two resonances indicating the presence of two diastereomers of the (E)-3-methyl-5-(2,2,3-trimethylcyclopent-3-en-1-yl)pent-4-en-2-one.

(The procedures described above is essentially that outlined in Chart II, Path B. Ketone 3 prepared via Path A would be free of the isomeric ethyl ketone 8. Also, if the starting ketone 2 was prepared from optically pure R- or S-campholenic aldehyde, as shown in U.S. Pat. No. 4,052,341, the asymmetric center that is part of the cyclopentyl ring would be fixed as R or S.)

EXAMPLE II

Preparation of
(E)-3-Methyl-5-(2,2,3-trimethylcylcopent-3-en-1-yl)pent-4-en-2-ol (1)

Ethanol (221 g, 280 ml), water (70 g) and 30% sodium hydroxide solution (1.0 ml) were added to a reaction flask. The mixture was stirred and sodium borohydride powder (12.9 g, 0.34 mole) was added in portions. The mixture was cooled to 0° C. and 116.2 g (0.56 mole) of a composition prepared as described in Example I containing (E)-3-methyl-5-(2,2,3-trimethylcyclopent-3-en-1-yl)pent-4-en-2-one (3) (87%) and the isomeric ethyl ketone 8 (8%) was added slowly over 1.0 hour at 0°–5° C.

The resultant mixture was stirred for 1.0 hour at 0° C. and then for 3.0 hours at ambient temperature. The mixture was poured into a beaker containing 400 ml of water and 40 ml of 30% sodium hydroxide solution and stirred well. The aqueous mixture was then extracted with three 125-ml portions of hexane. The hexane extracts were combined, washed with three 150-ml portions of water, dried over anhydrous magnesium sulfate, filtered and concentrated by distilling off the hexane at atmospheric pressure (760 mm).

The remaining oil was distilled at reduced pressure (0.9 mm) to give 103.9 g (94.5% yield) of (E)-3-methyl-5-(2,2,3-trimethylcyclopent-3-en-1-yl)pent-4-en-2-ol (1) and the ethyl isomer 9; GLC (Carbowax ®20M capillary column) shows 1 to be two peaks present at 51% and 36%, respectively, and 9 present at 7%; GLC (ethylene glycol succinate capillary column) shows 1 to be four peaks present at 27.5%, 27.0%, 19.5% and 19.5%, respectively, and 9 present at 6.5%; bp 93°–102° C. (0.9 mm); $n_D^{20}$ 1.481; mol. wt.

208 (MS): IR 3360 cm$^{-1}$ (hydroxyl), 3035 (olefinic), 1650 (olefinic) and 790 (trisubstituted olefin); Odor: very intense, creamy, woody, musk, sandalwood.

$^1$H-NMR 0.8δ(3H, s), 1.0(3H, s), 1.1(3H, d, J~7 Hz), 1.2(3H, d, J~7 Hz), 1.6(3H, broad s, olefinic CH$_3$), 1.9–2.6(5H, broad complex), 3.6(1H, broadened sextet), 5.2(1H, broad multiplet, ring olefinic proton), 5.1–5.8(2H, broad multiplet, 2 olefinic protons).

$^{13}$C-NMR 12.7 ppm(q), 16.0+16.7(2q), 20.1+20.3(2q), 20.5(q), 25.4+25.5(2q), 35.4(t), 44.1+44.4(2d), 45.2(d), 48.0(s), 54.1+54.3(2d), 70.1+71.0(2d), 122.5(d), 132.6+132.7(2d), 133.7(d) and 148.0(s). The $^{13}$C-NMR indicates 14 distinct carbon resonances with 7 carbon resonances appearing as two resonances indicating the presence of diastereomers.

EXAMPLE III

A. Separation and Purification of the Two Separable Components of (E)-3-Methyl-5-(2,2,3-trimethylcyclopent-3-en-1-yl)pent-4-en-2-ol (1a and 1b) and the Isomer (E)-6-(2,2,3-Trimethylcyclopent-3-en-1-yl)hex-5-en-3-ol (9)

The product prepared according to Example II was subjected to a spinning band distillation and the three components isolated in pure form and characterized by spectral analyses. The following results were obtained:

(1) (2R*,3S*)-(E)-3-Methyl-5-(2,2,3-trimethylcyclopent-3-en-1-yl)pent-4-en-2-ol(1a)

GLC (ethylene glycol succinate capillary column) two peaks present at 48.4% and 42.1%, respectively; bp 86.5° C. (0.95 mm); IR 3380 cm$^{-1}$ (hydroxyl), 3040 (olefinic), 1655 (olefinic), 800 (trisubstituted olefin); MS(m/e), 208(M$^+$, 1%), 164(66%), 149(84%), 121(100%), 109(50%), 108(99%), 93(82%), 83(50%), 55(93%), 45(84%), 43(63%), 41(80%); Odor Threshold Value 0.02 ng/l; Odor: powerful creamy, woody, musk, sandalwood.

$^1$H-NMR 0.8δ(3H, s), 1.0(3H, s), 1.02(3H, d, J~6 Hz), 1.2(3H, d, J~6.5 Hz), 1.6(3H, broad s, olefinic CH$_3$), 1.9–2.6(5H, broad complex), 3.6(1H, heptet, J~6.5 Hz), 5.3(1H, broad multiplet, ring olefinic proton), 5.1–5.9(2H, broad complex, 2 olefinic protons).

The $^1$H-NMR (400 MHz) spectrum is consistent with the structure of alcohol 1a and indicates a 1:1 mixture of diastereomeric alcohols.

$^{13}$C-NMR 12.7 ppm(q), 16.6(q), 20.0(q), 20.6(q), 25.5(q), 35.5(t), 45.0(t), 45.0(d), 48.0(s), 54.4(d), 71.0(d), 121.6(d), 132.8(d), 133.3(d), 147.9(s).

(2) (2R*,3R*)-(E)-3-Methyl-5-(2,2,3-trimethylcyclopent-3-en-1-yl)pent-4-en-2-ol (1b)

GLC (ethylene glycol succinate capillary column) two peaks present at 43.3% and 50.3%, respectively; bp 93.5° C. (1.20 mm); IR 3350 cm$^{-1}$ (hydroxyl), 3040 (olefinic), 1655 (olefinic) and 798 (trisubstituted olefin); MS(m/e), 208(M$^+$, absent), 164(82%), 149(86%), 121(100%), 109(48%), 108(95%), 107(96%), 93(79%), 83(51%), 55(90%), 45(81%), 43(60%), 41(75%); Odor Threshold Value 9.0 ng/l; Odor: woody, sandalwood, with fruity, vetiver acetate nuances.

$^1$H-NMR 0.8δ(3H, s), 1.0(3H, s), 1.1(3H, d, J~7 Hz), 1.2(3H, d, J~Hz), 1.6(3H, broad s), 1.9–2.5(4H, broad complex), 2.7(1H, broad s, exchanged with D$_2$O), 3.6(1H, multiplet, J~6 Hz), 5.3(1H, broad multiplet, ring olefinic proton), 5.1–5.5(2H, broad complex, 2 olefinic protons).

The $^1$H-NMR (400 MHz) spectrum is consistent with the structure of alcohol 1b and indicates a 1:1 mixture of diastereomeric alcohols.

$^{13}$C-NMR 12.6 ppm(q), 16.2(q), 20.2(q), 20.5(q), 25.5(q), 35.5(t), 44.5(d), 48.0(s), 54.4(d), 71.2(d), 121.6(d), 132.2(d), 132.8(d) and 147.9(s).

(3) (E)-6-(2,2,3-Trimethylcyclopent-3-en-1-yl)hex-5-en-3-ol (9)

bp 101.5° C. (1.40 mm); IR 3345 cm$^{-1}$ (hydroxyl), 3040 (olefinic) and 800 (trisubstituted olefin); MS(m/e) 208(M$^+$, 4%), 150(45%), 135(100%), 108(48%), 107(83%), 93(48%), 59(50%), 41(36%); Odor Threshold Value 47 ng/l; Odor: woody, ionone, with fruity, maple nuances.

$^1$H-NMR 0.8δ(3H, s), 0.95(3H, t, J~7 Hz), 1.0(3H, s), 1.1–1.7(2H, multiplet, J~6 Hz), 1.6(3H, broad s, olefinic CH$_3$), 1.9–2.7(6H, broad complex), 3.6(1H, broad multiplet, J~6 Hz), 5.3(1H, broad multiplet, ring olefinic H), 5.4–5.9(2H, broad complex, 2 olefinic protons).

The $^1$H-NMR (400 MHz) spectrum is consistent with the structure of alcohol 9 and indicates a 1:1 mixture of diastereomeric alcohols.

$^{13}$C-NMR 9.9 ppm(q), 12.7(q), 20.5(q), 25.5(q), 29.4(t), 35.5(t), 40.5(d), 47.9(s), 54.3(t), 72.4(d), 121.5(d), 126.9(d), 134.8(d), 147.9(s).

B. Identification of the Diastereomers of (E)-3-Methyl-5-(2,2,3-trimethylcyclopent-3-en-1-yl)pent-4-en-2-ol by X-Ray Diffraction Crystallography The product (70 g; 0.34 mole) prepared according to Example II was reacted with 60 g (0.36 mole) α-naphthyl isocyanate at 120°–130° C. The resultant mixture was cooled to ambient temperature and was dissolved in hexane (300 ml). The hexane solution was cooled to 0° C. in order to induce crystallization. The crystalline material was collected by filtration to give 57 g of solid α-naphthyl carbamate (mp 90°–97° C.). The filtrate was concentrated to give 70 g of viscous oil.

The crystalline carbamate was repeatedly recrystallized, first from t-butyl methyl ether, then from methanol and finally from t-butyl methyl ether to give 1.2 g of very pure crystalline α-naphthyl carbamate (mp 117.7°–117.9° C.) which was subjected to X-ray crystallographic analysis.

The X-ray analysis showed that this crystalline carbamate possessed the relative stereochemical configuration at C-2 and C-3 of R* and R* respectively. (See J. Rigaudy and S. P. Klesney, "Nomenclature of Organic Chemistry" 1979 Edition, Pergamon Press, New York, p. 482, for naming of chiral centers for which the relative configuration is known.) This diastereomer would therfore be a "syn" or "erythro" diastereomer namely a syn-(E)-3-methyl-5-(2,2,3-trimethylcyclopent-3-en-1-yl)pent-4-en-2-ol diastereomer. Since the X-ray analysis also determined the relative stereochemical configuration at the third chiral center, ring carbon 1, to be R*, this crystalline carbamate would be the (2R*,3R*)-(E)-3-methyl-5-(2,2,3-trimethylcyclopent-3-en-1(R*)-yl)-pent-4-en-2-ol diastereometer.

In order to isolate and correlate this crystalline carbamate to the component 1a or 1b, the pure solid was subjected to ester hydrolysis and the neutral fraction was isolated. Analysis by ¹H-NMR and GLC on the ethylene glycol succinate column (LAC-4R-886) showed this neutral fraction to be the third peak (99.5% pure) of 1, i.e., the first peak of the component 1b.

In light of the 400 MHz ¹H-NMR spectra of 1b which shows that the two diastereomers present in 1b are of similar relative configuration of C-2 and C-3 it can be deduced that the second component of 1b (fourth component of 1) would be the other possible syn diastereomer, namely, the (2R*,3R*)-(E)-3-methyl-5-(2,2,3-trimethylcyclopent-3-en-1(S*)-yl)pent-4-en-2ol diastereomer.

In order to obtain a crystalline ester of component 1a suitable for X-ray diffraction anayisis the viscous oil portion of the α-naphthyl carbamate (70 g) was distilled to separate the volatile material from any residue. The resultant volatile fraction (56 g) was hydrolyzed and the resultant neutral portion (23 g), a mixture of 70% 1a, 15% 1b and 15% impurities, was reacted with 3-nitrophthalic anhydride in the presence of pyridine at 80° C. for 1.0 hour. After workup and isolation there was obtained 31 g of crystalline 3-nitrophthalic acid mono ester (mp 118°–125° C.).

The mono ester was repeatedly recrystallized first from a 9 to 1 mixture of hexane/t-butyl methyl ether, then from a 9 to 1 mixture of methanol/water and finally from a mixture of carbon tetrachloride/hexane to give 1.2 g of very pure crystalline 3-nitrophthalic acid mono ester (mp 146.5° C.). The crystalline form of this mono ester was not suitable for X-ray diffraction analysis.

The mono ester (1.0 g) was therefore hydolyzed and the crude product (0.65 g) was distilled at 80° C. (0.07 mm) to yield 0.45 g of an oil identified by GLC (LAC-4R-886) as the first peak of 1, i.e., the first compoent of 1a. The oil (0.2 g) was then reacted with ca. 5% solution of isocyanic acid to form the allophonate. (See Helv. 35,2380 (1952); L. Fieser et al. "Reagents For Organic Synthesis", Vol I, John Wiley and Sons, Inc. New York, p. 170.) The reaction mixture was left at ambient temperatures for three days in an open flask, extracted with ether and washed with 10% potassium hydroxide solution. Evaporation gave 0.2 g of allophanate crystals which were recrystallized from ethanol to give 0.13 g allophanate (m.p. 154° C.). These crystals were suitable for X-ray diffraction analysis.

The X-ray analysis showed that this crystalline allophanate had the relative stereochemical configuration at C-2 and C-3 of R* and S* respectively. This diastereomer would therefore be an "anti" or "threo" diastereomer namely an anti-(E)-3-methyl-5(2,2,3-trimethylcyclopent-3-en-1-yl)pent-4-en-2-ol diastereomer. Since the X-ray analysis also determined the relative stereochemical configuration at the third chiral center, ring carbon 1, to be S* this crystalline allophonate would be the (2R*,3S*)-(E)-3-methyl-5-(2,2,3-trimethylcyclopent-3-en-1(S*)-yl)pent-4-en-2-ol diastereomer.

In light of the 400 MHz ¹H-NMR spectra of 1a which shows that the two diastereomers present in 1a are of similar relative configuration at C-2 and C-3 it can be deduced that the second component of 1a (second component of 1) would be the other possible anti diastereomer, namely the (2R*,3S*)-(E)-3-methyl-5-(2,2,3-trimethyl-3-en-1(R*)-yl)pent-4-en-2-ol diastereomer.

The four isomers as they elute from the GLC (LAC-4R-886) are as follows:
1. (2R*,3S*)-(E)-3-methyl-5-(2,2,3-trimethylcyclopent-3-en-1(S*)-yl)pent-4-en-2-ol,
2. (2R*,3S*)-(E)-3-methyl-5-(2,2,3-trimethylcyclopent-3-en-1(R*)-yl)pent-4-en-2-ol,
3. (2R*,3R*)-(E)-3-methyl-5-(2,2,3-trimethylcyclopent-3-en-1(R*)-yl)pent-4-en-2-ol, and,
4. (2R*,3R*)-(E)-3-methyl-5-(2,2,3-trimethylcyclopent-3-en-1(S*)pent-4-en-2-ol.

An odor threshold value comparision of the two diastereomers of 1a indicates that the (2R*,3S*)-(E)-3-methyl-5-(2,2,3-trimethylcyclopent-3-en-1(R*)-yl)pent-4-en-2-ol is the stronger of the two diastereomers by a factor of about 10.

EXAMPLES IV AND V

These examples illustrate novel homoallylic alcohols structurally related to 1 [i.e., 2-methyl-4-(2,2,3-trimethylcyclopent-3-en-1-yl)but-3-en-1-ol and 5-(2,2,3-trimethylcyclopent-3-en-1-yl)pent-4-en-2-ol] which were found to possess properties very different than 1.

EXAMPLE IV

Preparation of
2-Methyl-4-(2,2,3-trimethylcyclopent-3-en-1-yl)but-3-en-1-ol

The aldehyde, 2-methyl-4-(2,2,3-trimethylcyclopent-3-en-1-yl)but-2-enal, which had been prepared by using the procedure outlined in U.S. Pat. No. 4,052,341 Example IV-1, was reacted essentially following the procedure described in Example I for isomerizing the α,β double bond to the β,γ position. In this case the butenal (19.2 g, 0.1 mole) was reacted with potassium t-butoxide (16.8 g, 0.15 mole) in 1,2-dimethoxyethane (DME, 200 ml) at 15°–20° C. by feeding in the butenal over 30 minutes, stirring for an additional 15 minutes and then rapidly quenching with aqueous 20% acetic acid (75 ml).

After work-up, the crude oil was distilled at reduced pressure to yield 14.6 g of distillate: bp 68°–100° (0.6 mm). The distillate was a mixture having the following composition as determined by GC/MS analysis:

29% 2-methyl-4-(2,2,3-trimethylcyclopent-3-en-1-yl)but-3-enal

57% 2-methyl-4-(2,2,3-trimethylcyclopent-3-en-1-yl)but-2-enal (26% Z-isomer, 31% E-isomer)

The above mixture (17.0 g, 88.5 mmoles) of aldehydes was dissolved in anhydrous ethyl ether (25 ml) and was slowly fed into a flask containing a cold (0° C.) suspension of lithium aluminum hydride (1.7 g, 44.3 mmole) in anhydrous ether (25 ml).

The resultant mixture was stirred for 30 minutes at 0°–5° C., then for 1.0 hour at ambient temperature and then at reflux for 2.0 hours. The mixture was then cooled to 0° C. and the excess lithium aluminum hydride was decomposed carefully by the slow, dropwise addition of saturated aqueous sodium sulfate solution.

The resultant suspension was filtered, the ether removed by distillation at atmospheric pressure and the remaining oil distilled under reduced pressure to give 14.0 g of distillate: bp 89°–145° C. (0.9 mm); a mixture of components by GC/MS consisting of:

22% 2-methyl-4-(2,2,3-trimethylcyclopent-3-en-1-yl)but-3-en-1-ol

71% 2-methyl-4-(2,2,3-trimethylcyclopent-3-en-1yl)-but-2-en-1-ol (27% Z-isomer, 44% E-isomer)

This mixture was subjected to a careful spinning band distillation to give:

2-methyl-4-(2,2,3-trimethylcyclopent-3-en-1-yl)but-3-en-1-ol: bp 76.5° C. (0.5 mm); mol. wt. 194 (MS); IR 3340 cm$^{-1}$ (hydroxyl), 3040, 1670 and 800 (olefinic); Odor Threshold Value 6.0 ng/l; Odor: fruity, woody, anisic.

$^1$N-NMR 0.8δ(3H, s), 1.0(3H, s), 1.2(3H, d, J~6 Hz), 1.6(3H, broad s, olefinic CH$_3$), 2.2 and 2.4(5H, 2 broad complexes), 3.4(2H, d, J~7 Hz), 5.2(1H, broad multiplet), 5.0–5.8(2H, broad complex, olefinic protons).

$^{13}$C-NMR 12.7 ppm(q), 16.8+17.0(2q, C-2 methyl group), 20.5(q), 25.4(q), 35.5(t), 39.7(d), 47.9(s), 54.2(d), 67.5(t, C-1), 121.5(d), 132.3(d), 133.1+133.2(2d, C-3), 147.9(s). The $^{13}$C-NMR shows 13 distinct carbon resonances with 2 carbon resonances appearing as two resonances indicating the presence of diastereomers. This molecule contains two asymmetric carbon atoms; that is, C-2 of the side-chain and C-1 of the cyclopentenyl ring.

EXAMPLE V

Preparation of 5-(2,2,3-Trimethylcyclopent-3-en-1-yl)-pent-4-en-2-ol

The ketone, 5-(2,2,3-trimethylcyclopent-3-en-1-yl)pent-3-en-2-one, which had been prepared by using the procedure of U.S. Pat. No. 4,052,341, Example II-2, was reacted essentially following the procedure described in Example I for isomerizing the α,β double bond to the β,γ position. In this case the ketone (28.8 g, 0.15 mole) was reacted with potassium t-butoxide (25.8 g, 0.23 mole) in 1,2-dimethoxyethane (DME) (125 ml). The reaction was quenched by addition of aqueous 20% acetic acid (115 ml), extracted as in Example I and the oil distilled at reduced pressure to yield 19.0 g (66% yield) of 5-(2,2,3-trimethylcyclopent-3-en-1-yl)pent-4-en-2-one as a mixture of Z- (21%) and E- (69%) isomers: bp 80°–100° C. (0.5 mm); mol. wt. 192 (MS); IR 3040 cm$^{-1}$ (olefin), 1720 (carbonyl), 800 (trisubstituted olefin).

$^1$H-NMR 0.8δ(3H, s), 1.0(3H, s), 1.6(3H, broad s, olefinic CH$_3$), 2.2(3H, s, acetyl CH$_3$), 1.9–2.7(3H, broad complex), 3,1(1H, d, J~6 Hz), 3.2(1H, d, J~6 Hz), 5.2(1H, broad multiplet, ring olefinic CH$_3$), 5.6(2H, broad multiplet, 2 olefinic H).

$^{13}$C-NMR 12.6 ppm(q), 20.5(q), 25.4(q), 29.1(q), 35.3(t), 42.5(s), 48.2(d), 54.1(t), 121.5(d), 122.8(d), 135.9(d), 147.8(s), 206.4(s, carbonyl). The presence of the Z-isomer as a minor component was indicated by weaker carbon resonances at 20.3(q), 25.9(q), 29.3(q), 36.0(t), 48.2, 48.7, 121.6(d), 121.9(d), 134.6(d), 205.9(s, carbonyl).

The ratio of the two carbonyl carbon resonances indicated a 72%/28% mixture, which is in good agreement with the GLC assay.

Using the procedure as outlined in Example II, 5-(2,2,3-trimethylcyclopent-3-en-1-yl)pent-4-en-2-one (14.4 g, 75 mmoles) are reacted with sodium borohydride powder (1.44 g, 38 mmoles) in a mixture of ethanol (75 ml), water (15 ml) and 30% sodium hydroxide solution (0.25 ml).

The mixture was quenched, worked up and distilled to give 12.4 g (85.2% theory-yield) of 5-(2,2,3-trimethylcyclopent-3-en-1-yl)pent-4-en-2-ol as a mixture of Z- (23%) and E- (69%) isomers: bp 79°–81° C. (0.5 mm); n$_D^{20}$ 1.4820; mol. wt. 194 (MS); IR 3340 cm$^{-1}$ (hydroxyl), 3040 (olefinic), 1655 (olefinic) and 800 (trisubstituted olefin); Odor Threshold Value 720 ng/l; Odor: weak, sandalwood, woody.

$^1$H-NMR 0.7δ(3H, s), 1.0(3H, s), 1.2(3H, d, J~6 Hz), 1.6(3H, broad s, olefinic CH$_3$), 2.2(5H, broad multiplet), 3.1'(1H, broad, exchanges with D$_2$O, hydroxyl H), 3.8(1H, broad sextet, J~6 Hz), 5.2(1H, broad multiplet, ring olefinic H), 5.5(2H, broad complex, 2 olefinic protons).

$^{13}$C-NMR 12.6 ppm(q), 20.5(q), 22.6(q), 25.5(q), 35.5(t), 42.8(s), 47.9(d), 54.3(t), 67.4(d), 121.6(d), 127.0(d), 134.2(d), 147.7(s). The presence of the Z-isomer as a minor component was indicated by the following carbon resonances: 25.9(q), 36.4, 37.4, 48.5, 48.6, 67.6(d), 126.6(d), 133.3(d).

EXAMPLE VI

The following fragrance compositions illustrate the odorant utility of (E)-3-methyl-5-(2,2,3-trimethylcyclopent-3-en-1-yl)pent-4-en-2ol (1), as prepared in Example II. In each instance the effects achieved with 1 could not be achieved with similar amounts of sandalwood oil or 3-methyl-5-(2,2,3-trimethylcyclopent-3-en-1-yl)pentan-2-ol (12) due to the unique odor intensity of 1.

| A. Chypre Base | |
|---|---|
| Component | Parts |
| Bergamot Oil (non-sensitizing; furanocoumarin-free) | 300 |
| Rose Base synthetic (mainly phenylethyl alcohol, citronellol, geraniol) | 400 |
| Acetyl Cedrene | 200 |
| Oakmoss Soluble Resin | 60 |
| Vetiver Bourbon | 20 |
| Dipropylene Glycol | 15 |
| TOTAL | 995 |

Addition of 5 parts (0.5%) of 1 to the chypre base improves the strength and the warm woody quality of the fragrance. (A similar effect can be obtained by using 3 parts of component 1a.) In the absence of the addition of 1 or 1a, the composition lacks the warm, musky-sandalwood note characteristic of 1 and 1a. A similar amount of sandalwood oil makes very little contribution to the fragrance.

B. Wood Base

| Component | Parts |
|---|---|
| Sandela ® (Givaudan)(Isocamphyl-cyclohexanols) 50% in Diethyl Phthalate | 300 |
| Acetyl Cedrene | 450 |
| Cedrol Crystals | 200 |
| Gamma-Nonalactone | 2 |
| DiPropylene Glycol | 25 |
| TOTAL | 975 |

Addition of 25 parts (2.5%) of 1 to the wood base blends the cedar and the sandalwood notes, and adds body and a warm musk quality to the fragrance, while greatly increasing the strength. (A similar effect can be achieved using 15 parts of 1a in place of 1.) Without the addition of 1 or 1a, the composition is not as full or as strong and lacks the musk note characteristic of 1 and 1a. A similar amount of sandalwood oil results in a composition that is less intense and less musky.

C. Muguet Base

| Component | Parts |
|---|---|
| Citronellol Synthetic | 200 |
| Phenylethyl Alcohol | 100 |
| Lilial ® (Givaudan)(α-methyl-p-tert-butyl-phenylpropionaldehyde) | 200 |
| Terpineol Synthetic | 50 |
| Linalool | 100 |
| Benzyl Acetate | 100 |
| Hexylcinnamic Aldehyde | 150 |
| Indole, 10% in Dipropylene Glycol | 10 |
| Cyclamen Aldehyde(α-methyl-p-isopropyl-phenylpropionaldehyde) | 10 |
| Styrax (Natural, non-sensitizing) | 30 |
| Dipropylene Glycol | 47 |
| TOTAL | 997 |

Addition of 3 parts (0.3%) of 1 to the muguet base blends the individual floral components and adds body, fullness and warmth to the fragrance. (Addition of about 2 parts of 1a in place of 1 provides a similar effect.) Without the addition of 1 or 1a the composition lacks unity and fullness. The same effects cannot be achieved with the addition of sandalwood oil or compound 12.

D. Musk Fragrance

| Component | Parts |
|---|---|
| Coumarin | 10 |
| Heliotropin | 35 |
| Vanillin | 2 |
| Benzyl Acetate | 10 |
| Methyl Dihydrojasmonate | 10 |
| Bergamot Synthetic | 40 |
| Dimetol ® (Givaudan) (2,6-dimethylheptan-2-ol) | 5 |
| Geranium Oil | 25 |
| Rose Base Synthetic (mainly phenylethyl alcohol, citronellol, geraniol) | 10 |
| Lavender Oil | 25 |
| Lemon Oil, California | 20 |
| Lilial ® (Givaudan) (α-methyl-p-tert-butylphenylpropionaldehyde) | 10 |
| Oakmoss, Soluble Resin | 5 |
| Folenox ™ (Givaudan) (isolongifolene epoxide) | 25 |
| Ethylene Brassylate | 200 |
| Fixolide ® (Givaudan) (7-acetyl-1,1,3,4,4,6-hexamethyltetralin) | 200 |
| Amyl Salicylate | 40 |
| Dipropylene Glycol | 278 |
| TOTAL | 950 |

Addition of 50 parts (5.0%) of 1 to the musk fragrance greatly increases the strength of the fragrance while improving both the intensity and the quality of the musk notes. (A similar effect can be achieved using 30 parts of 1a). The same effect cannot be achieved using sandalwood oil or compound 12.

I claim:

1. A mixture of isomers of 3-methyl-5-(2,2,3-trimethylcyclopent-3-en-1-yl)pent-4en-2-ol comprising at least ten percent (2R*,3S*)-(E)-3-methyl-5-(2,2,3-trimethylcyclopent-3-en-1-yl)pent-4-en-2-ol.

2. A mixture of isomers according to claim 1 wherein the (2R*,3S*)-(E)-3-methyl-5-(2,2,3-trimethylcyclopent-3-en-1-yl)pent-4-en-2-ol comprises at least twenty-five percent of the total mixture.

3. A mixture of isomers according to claim 1 wherein the (2R*,3S*)-(E)-3-methyl-5-(2,2,3-trimethylcyclopent-3-en-1-yl)pent-4-en-2-ol comprises at least forty percent of the total mixture.

4. A mixture of isomers according to claim 1 wherein the (2R*,3S*)-(E)-3-methyl-5-(2,2,3-trimethylcyclopent-3-en-1-yl)pent-4-en-2-ol comprises at least fifty percent of the total mixture.

5. A mixture of isomers according to claim 1 wherein the (2R*,3S*)-(E)-3-methyl-5-(2,2,3-trimethylcyclopent-3-en-1-yl)pent-4-en-2-ol comprises at least ninety percent of the total mixture.

6. A mixture of isomers according to claim 4 which consists essentially of
   (a) fifty to one hundred percent (2R*,3S*)-(E)-3-methyl-5-(2,2,3-trimethylcyclopent-3-en-1-yl)-pent-4-en-2-ol,
   (b) zero to forty-five percent (2R*,3R*)-(E)-3-methyl-5-(2,2,3-trimethylcyclopent-3-en-1-yl)-pent-4-en-2-ol,
   (c) zero to twelve percent (E)-6-(2,2,3-trimethylcyclopent-3-en-1-yl)hex-5-en-3-ol,
   (d) zero to ten percent 3-methyl-5-(2,2,3-trimethylcyclopent-3-en-1-yl)pent-3-en-2-ol, and,
   (e) zero to ten percent 3-methyl-5-(2,2,3-trimethylcyclopent-3-en-1-yl)pentan-2-ol.

7. A mixture of isomers according to claim 3 which consists essentially of
   (a) forty to sixty-five percent (2R*,3S*)-(E)-3-methyl-5-(2,2,3-trimethylcyclopent-3-en-1-yl)-pent-4-en-2-ol,
   (b) twenty-five to forty-five percent (2R*,3R*)-(E)-3-methyl-5-(2,2,3-trimethylcyclopent-3-en-1-yl)-pent-4-en-2-ol,
   (c) zero to twelve percent (E)-6-(2,2,3-trimethylcyclopent-3-en-1-yl)hex-5-en-3ol,
   (d) zero to five percent 3-methyl-5-(2,2,3-trimethylcyclopent-3-en-1-yl)pent-3-en-2-ol, and,
   (e) zero to five percent 3-methyl-5-(2,2,3-trimethylcyclopent-3-en-1-yl)pentan-2-ol.

8. A mixture of isomers according to claim 7 wherein
   (a) said (2R*,3S*)-(E)-3-methyl-5-(2,2,3-trimethylcyclopent-3-en-1-yl)pent-4-en-2-ol is present at a level of forty-five to sixty percent, (b) said (2R*,3R*)-(E)-3-methyl-5-(2,2,3-trimethylcyclopent-3-en-1yl)pent-4-en-2-ol is present at a level of thirty to forty-five percent, and, (c) said (E)-6-(2,2,3-trimethylcyclopent-3-en-1-yl)hex-5-en-3-ol is present at a level of less than ten percent.

9. A fragrance composition to which there has been added as a fragrance contributing ingredient, a composition comprising at least ten percent (2R*,3S*)-(E)-3-methyl-5-(2,2,3-trimethylcyclopent-3-en-1-yl)pent-4en-2-ol.

10. A fragrance composition according to claim 9 wherein (2R*,3S*)-(E)-3-methyl-5-(2,2,3-trimethylcyclopent-3-en-1-yl)pent-4-en-2-ol comprises at least twenty-five percent of said fragrance contributing ingredient added.

11. A fragrance composition according to claim 10 wherein (2R*,3S*)-(E)-3-methyl-5-(2,2,3-trimethylcyclopent-3-en-1-yl)pent-4-en-2-ol comprises at least forty percent of said fragrance contributing ingredient added.

12. A fragrance composition according to claim 11 wherein (2R*,3S*)-(E)-3-methyl-5-(2,2,3-trimethylcyclopent-3-en-1-yl)pent-4-en-2-ol comprises at least fifty percent of said fragrance contributing ingredient added.

13. A fragrance composition according to claim 12 wherein (2R*,3S*)-(E)-3-methyl-5-(2,2,3-trimethylcyclopent-3-en-1-yl)pent-4-en-2-ol comprises at least ninety percent of said fragrance contributing ingredient added.

14. A fragrance composition according to claim 11 to which there has been added as a fragrance contributing ingredient, a composition consisting essentially of
  (a) forty to one hundred percent (2R*,3S*)-(E)-3-methyl-5-(2,2,3-trimethylcyclopent-3-en-1-yl)pent-4-en-2-ol,
  (b) zero to forty-five percent (2R*,3R*)-(E)-3-methyl-5-(2,2,3-trimethylcyclopent-3-en-1-yl)pent-4-en-2-ol,
  (c) zero to twelve percent (E)-6-(2,2,3-trimethylcyclopent-3-en-1-yl)hex-5-en-3-ol,
  (d) zero to ten percent 3-methyl-5-(2,2,3-trimethylcyclopent-3-en-1-yl)pent-3-en-2-ol, and,
  (e) zero to ten percent 3-methyl-5-(2,2,3-trimethylcyclopent-3-en-1-yl)pentan-2-ol.

15. A fragrance composition according to claim 14 to which there has been added as a fragrance contributing ingredient, a composition consisting essentially of
  (a) forty to sixty-five percent (2R*,3S*)-(E)-3-methyl-5-(2,2,3-trimethylcyclopent-3-en-1-yl)pent-4-en-2-ol,
  (b) twenty-five to forty-five percent (2R*,3R*)-(E)-3-methyl-5-(2,2,3-trimethylcyclopent-3-en-1-yl)pent-4-en-2-ol,
  (c) zero to twelve percent (E)-6-(2,2,3-trimethylcyclopent)-3-en-1-yl)hex-5-en-3-ol,
  (d) zero to five percent 3-methyl-5-(2,2,3-trimethylcyclopent-3-en-1-yl)pent-3-en-2-ol, and,
  (e) zero to five percent 3-methyl-5-(2,2,3-trimethylcyclopent-3-en-1-yl)pentan-2-ol.

16. A fragrance composition according to claim 15 wherein
  (a) said (2R*,3S*)-(E)-3-methyl-5-(2,2,3-trimethylcyclopent-3-en-1-yl)pent-4-en-2-ol is present at a level of forty-five to sixty percent,
  (b) said (2R*,3R*)-(E)-3-methyl-5-(2,2,3-trimethylcyclopent-3-en-1-yl)pent-4-en-2-ol is present at a level of thirty to forty-five percent, and,
  (c) said (E)-6-(2,2,3-trimethylcyclopent-3-en-1-yl)hex-5-en-3-ol is present at a level of less than ten percent.

17. A fragrance composition according to claims 12, 13, 14, 15 or 16 wherein there is added an amount such that the concentration of (2R*,3S*)-(E)-3-methyl-5-(2,2,3-trimethylcyclopent-3-en-1-yl)pent-4-en-2-ol is between 0.05% and 25% of the total fragrance imparting ingredients.

18. A fragrance composition according to claim 17 wherein there is added an amount such that the concentration of (2R*,3S*)-(E)-3-methyl-5-(2,2,3-trimethylcyclopent-3-en-1-yl)pent-4-en-2-ol is between 0.1% and 10% of the total fragrance imparting ingredients.

19. A method for improving a fragrance composition which comprises adding thereto an olefactorily effective amount of a composition comprising at least twenty-five percent (2R*,3S*)-(E)-3-methyl-5-(2,2,3-trimethylcyclopent-3-en-1-yl)pent-4-en-2-ol.

20. A method according to claim 19 wherein the material added is at least forty percent (2R*,3S*)-(E)-3-methyl-5-(2,2,3-trimethylcyclopent-3-en-1-yl)pent-4-en-2-ol.

21. A method according to claim 20 wherein the material added is at least fifty percent (2R*,3S*)-(E)-3-methyl-5-(2,2,3-trimethylcyclopent-3-en-1-yl)pent-4en-2-ol.

22. A method according to claim 21 wherein the material added is at least ninety percent (2R*,3S*)-(E)-3-methyl-5-(2,2,3-trimethylcyclopent-3-en-1-yl)pent-4-en-2-ol.

23. A method according to claim 20 wherein the material added consists essentially of
  (a) forty to one hundred percent (2R*,3S*)-(E)-3-methyl-5-(2,2,3-trimethylcyclopent-3-en-1-yl)pent-4-en-2-ol,
  (b) zero to forty-five percent (2R*,3R*)-(E)-3-methyl-5-(2,2,3-trimethylcyclopent)-3-en-1-yl)pent-4-en-2-ol,
  (c) zero to twelve percent (E)-6-(2,2,3-trimethylcyclopent-3-en-1-yl)hex-5-en-3-ol,
  (d) zero to ten percent 3-methyl-5-(2,2,3-trimethylcyclopent-3-en-1-yl)pent-3-en-2-ol, and,
  (e) zero to ten percent 3-methyl-5-(2,2,3-trimethylcyclopent-3-en-1-yl)pentan-2-ol.

24. A method according to claim 23 wherein the material added consists essentially of
  (a) forty to sixty-five percent (2R*,3S*)-(E)-3-methyl-5-(2,2,3-trimethylcyclopent-3-en-1-yl)-pent-4-en-2-ol,
  (b) twenty to forty-five percent (2R*,3R*)-(E)-3-methyl-5-(2,2,3-trimethylcyclopent-3-en-1-yl)-pent-4-en-2-ol,
  (c) zero to twelve percent (E)-6-(2,2,3-trimethylcyclopent-3-en-1-yl)hex-5-en-3-ol,
  (d) zero to five percent 3-methyl-5-(2,2,3-trimethylcyclopent-3-en-1-yl)pent-3-en-2-ol, and,
  (e) zero to five percent 3-methyl-5-(2,2,3-trimethylcyclopent-3-en-1-yl)pentan-2-ol.

25. A method according to claim 24 wherein
  (a) said (2R*,3S*)-(E)-3-methyl-5-(2,2,3-trimethylcyclopent-3-en-1-yl)pent-4-en-2-ol is present at a level of forty-five to sixty percent,
  (b) said (2R*,3R*)-(E)-3-methyl-5-(2,2,3-trimethylcyclopent-3-en-1-yl)pent-4-en-2-ol is present at a level of thirty to forty-five percent, and, (c) said (E)-6-(2,2,3-trimethylcyclopent-3-en-1-yl)hex-5-en-3-ol is present at a level of less than ten percent.

26. A method according to claims 21, 22, 23, 24 or 25 wherein there is added an amount such that (2R*,3S*)-(E)-3-methyl-5-(2,2,3-trimethylcyclopent-3-en-1-yl)pent-4-en-2-ol is between 0.05% and 25% of the total fragrance imparting ingredients.

27. A method according to claim 26 wherein there is added an amount such that the concentration of (2R*,3S*)-(E)-3-methyl-5-(2,2,3-trimethylcyclopent-3-en-1-yl)pent-4-en-2-ol is between 0.1% and 10% of the total fragrance imparting ingredients.

* * * * *